(12) United States Patent
Bowers

(10) Patent No.: US 9,687,665 B2
(45) Date of Patent: *Jun. 27, 2017

(54) SYSTEM AND METHOD FOR PERFORMING SELF-TEST IN AN AUTOMATIC EXTERNAL DEFIBRILLATOR (AED)

(71) Applicant: Scion Medical Limited, Mong Kok (HK)

(72) Inventor: Kyle R. Bowers, Boxborough, MA (US)

(73) Assignee: Scion Medical Limited, Mong Kok (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/686,121

(22) Filed: Apr. 14, 2015

(65) Prior Publication Data

US 2016/0067505 A1    Mar. 10, 2016

Related U.S. Application Data

(63) Continuation of application No. 11/282,186, filed on Nov. 18, 2005, now Pat. No. 9,008,767.

(60) Provisional application No. 60/629,054, filed on Nov. 18, 2004.

(51) Int. Cl.
*A61N 1/39* (2006.01)
*A61N 1/04* (2006.01)

(52) U.S. Cl.
CPC .......... *A61N 1/3925* (2013.01); *A61N 1/046* (2013.01); *A61N 1/3993* (2013.01)

(58) Field of Classification Search
CPC ..... A61N 1/3925; A61N 1/3993; A61N 1/046
See application file for complete search history.

(56) References Cited

U.S. PATENT DOCUMENTS

| | | | |
|---|---|---|---|
| 5,645,571 A | 7/1997 | Olson et al. | |
| 5,879,374 A | 3/1999 | Powers et al. | |
| 5,897,576 A * | 4/1999 | Olson et al. | 607/5 |
| 5,899,926 A | 5/1999 | Ochs et al. | |
| 6,073,085 A | 6/2000 | Wiley et al. | |
| 6,128,530 A | 10/2000 | Galen et al. | |
| 6,313,609 B1 | 11/2001 | Brink | |
| 6,329,822 B1 | 12/2001 | Powers | |
| 6,438,417 B1 | 8/2002 | Rockwell et al. | |
| 7,437,644 B2 | 10/2008 | Ginggen et al. | |
| 9,008,767 B2 * | 4/2015 | Bowers | A61N 1/3925 607/5 |
| 2003/0149455 A1 | 8/2003 | Obel et al. | |
| 2003/0212311 A1 * | 11/2003 | Nova et al. | 600/300 |
| 2005/0177198 A1 | 8/2005 | Norton et al. | |

\* cited by examiner

*Primary Examiner* — Rex R Holmes
(74) *Attorney, Agent, or Firm* — Pandiscio & Pandiscio

(57) ABSTRACT

An automatic external defibrillator with an intelligent self-test system that ensures device readiness. The self-test system conditionally runs functional tests based on knowledge of device use, time of day, pre-programmed information, operational features and previous events. The condition of the defibrillator is indicated visually, audibly or both based on the results of the self-test performed.

20 Claims, 8 Drawing Sheets

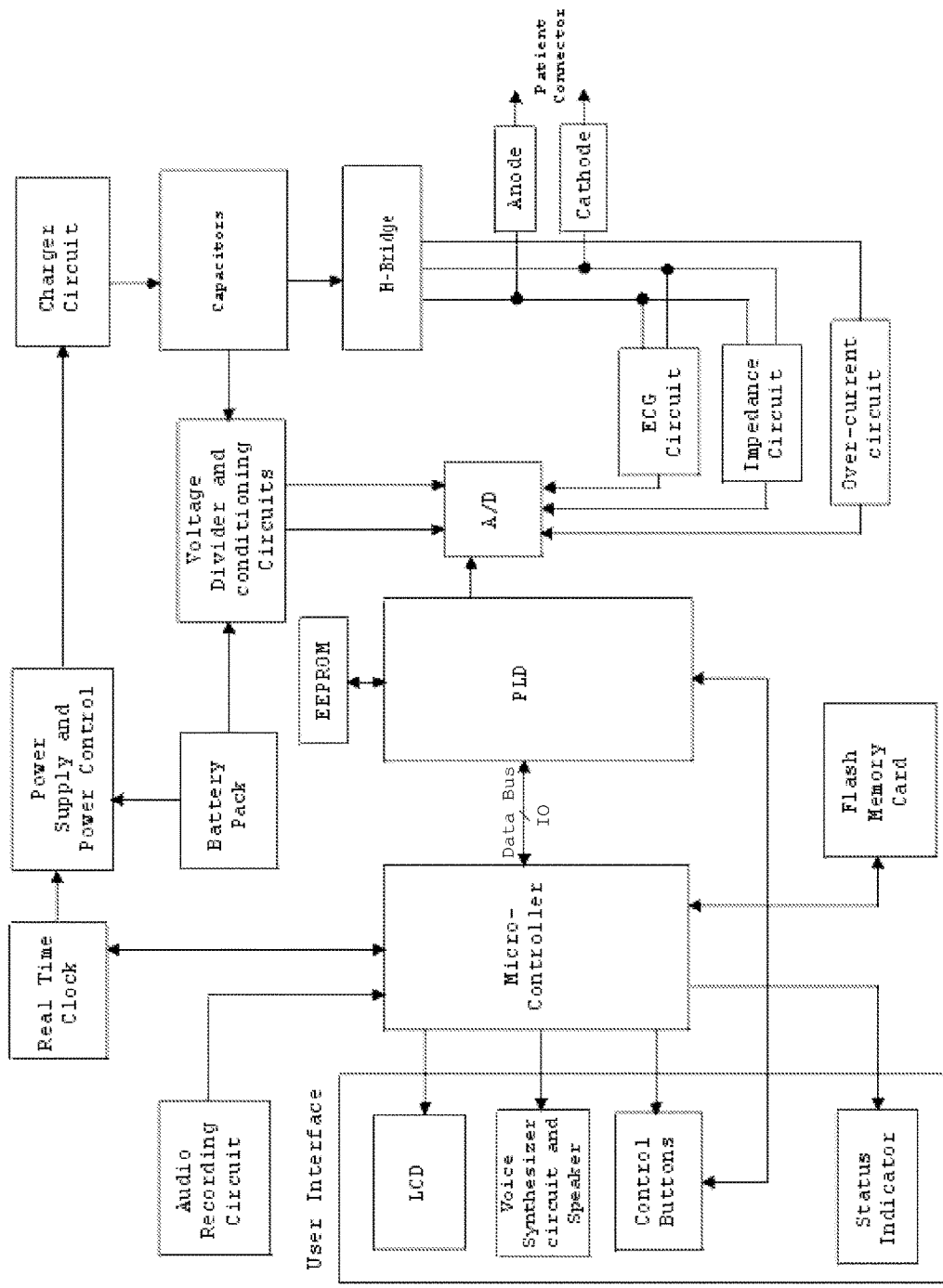
Fig. 2 System Block Diagram

Fig. 3 Self-Test Table and Error Codes

| Error Code | Device Tests1 | Analog Tests | Battery Switch Test | Reset Alarm Test | Power Control | Standby Wakeup1 | Device Tests2 | Standby Wakeup2 | Defib1 | Therapy Circuit | Cap Charge |
|---|---|---|---|---|---|---|---|---|---|---|---|
|  | ~12 ms. | ~1 ms. | ~60 ms. | ~1 ms. | ~6 ms. | ~12 ms. | ~762 ms | ~242 ms. | ~16 ms. | ~0 ms. | ~45 ms. |
|  | POWERON DAILY 1/4 | POWERON DAILY 1/4 | POWERON DAILY 1/4 | POWERON DAILY 1/4 | POWERON | POWERON | POWERON DAILY 1/4 | POWERON | POWERON DAILY 1/4 | POWERON DAILY 1/4 | - |
|  | Test ID 1 | Test ID 3 | Test ID 4 | Test ID 2 | Test ID 6 | Test ID 7 | Test ID 1 | Test ID 7 | Test ID 8 | Test ID 5 | Test ID 10 |
| 0x0001 | RESET FAIL | RESET FAIL | RESET FAIL | RESET FAIL | RESET FAIL | RESET FAIL | - | - | RESET FAIL | RESET FAIL | RESET FAIL |
| 0x0002 | MEMORY | NO 1MS | OVR SWBAT | START FPGA WDT | IRQ 2 LEVEL | TURNOFF 3V | - | - | START 1 MS | OVR GATE | CHARGER ENABLED* |
| 0x0004 | RAM | NO DATA | CHARGER EN | START RESET SIG | TURNOFF 3V | START TURNON | - | - | START DEFIB VALUE | 3VSW RETURN | NO V1 |
| 0x0008 | STACK | ADC REF | SHOCK START | START TURNOFF | TURNOFF | ALM SYNC TIMEOUT | - | - | START SYS FAULT | OVR GATE ENABLED | NO V2 |
| 0x0010 | STACK OVERFLOW | TEMP ERR | SWBAT CHG | RESET SIG HI | TURNON | - | - | TURNOFF | ENABLE DEFIB 1 | OVR GATE DISABLED | V2 LOW |
| 0x0020 | - | - | BV DROP | RESET SIG LO | - | - | CHECKS UM | TURNON | ENABLE SYSFAULT | - | V2 HIGH |
| 0x0040 | BUTTON | - | - | RESET SIG HI LAST | - | - | - | - | DISABLE DEFIB 1 | - | - |
| 0x0080 | RTC | - | - | - | - | - | - | - | DISABLE SYSFAULT | - | - |
| 0x0100 | MMC | - | - | - | - | - | - | - | - | - | - |
| 0x0200 | EEPROM | - | - | - | - | - | - | - | - | - | - |
| 0x0400 | AUDIO | - | - | - | - | - | - | - | - | - | - |
| 0x0800 | SOUND REC | - | - | - | - | - | - | - | - | - | - |
| 0x1000 | NO MMC * | - | - | - | - | - | - | - | - | - | - |
| 0x2000 | OLD BATT | - | - | - | - | - | - | - | - | - | - |
| 0x4000 | OLD TRAY | - | - | - | - | - | - | - | - | - | - |

Fig. 4 Schedule Of Self-Tests

| Schedule | Test Items |
|---|---|
| 1 | Analog To Digital Converter Tests<br>Analog Tests<br>Temperature Tests<br>Capacitor Charger Circuit Tests<br>Battery Capacity Tests |
| 2 | Device Tests:<br>• RAM<br>• Stack<br>• Buttons<br>• Real Time Clock<br>• Flash Card<br>• EEPROM<br>• Audio Recording<br>• Voice Playback<br>• Battery Expiration<br>• Pads Expiration<br>• Stack Overflow<br>• ROM Checksum |
| 3 | Battery Voltage<br>Battery Switch Tests<br>Monitor Circuit Tests |
| 4 | Defibrillator Over-current Tests<br>Therapy Circuit Tests |

SYSTEM AND METHOD FOR PERFORMING SELF-TEST IN AN AUTOMATIC EXTERNAL DEFIBRILLATOR (AED)

REFERENCE TO PENDING PRIOR PATENT APPLICATION

This patent application is a continuation of prior U.S. patent application Ser. No. 11/282,186, now U.S. Pat. No. 9,008,767, filed Nov. 18, 2005 by Kyle R. Bowers for SYSTEM AND METHOD FOR PERFORMING SELF-TEST IN AN AUTOMATIC EXTERNAL DEFIBRILLATOR (AED), which in turn claims benefit of prior U.S. Provisional Patent Application Ser. No. 60/629,054, filed Nov. 18, 2004 by Kyle R. Bowers for SYSTEM AND METHOD FOR PERFORMING SELF-TEST IN AN AUTOMATIC EXTERNAL DEFIBRILLATOR.

FIELD OF THE INVENTION

The present invention relates generally to a system and method for performing self-test in an automatic external defibrillator (AED).

BACKGROUND OF THE INVENTION

Approximately 350,000 deaths occur each year in the United States alone due to sudden cardiac arrest (SCA). Worldwide deaths due to SCA are believed to be at least twice that of the U.S. incidence. Many of these deaths can be prevented if effective defibrillation is administered within 3-5 minutes of the onset of SCA.

SCA is the onset of an abnormal heart rhythm, lack of pulse and absence of breath, leading to a loss of consciousness. If a normal pulse is not restored within a few minutes, death typically occurs. Most often, SCA is due to ventricular fibrillation (VF), which is a chaotic heart rhythm that causes an uncoordinated quivering of the heart muscle. The lack of coordinated heart muscle contractions results in inadequate blood flow to the brain and other organs. Death typically ensues unless this chaotic rhythm is terminated, allowing the heart to restore its own normal rhythm.

Rapid defibrillation is the only effective means to restore the normal heart rhythm and prevent death after SCA due to ventricular fibrillation. For each minute that passes after the onset of SCA, the rate of mortality generally increases by 10%. If the heart is defibrillated within 1-2 minutes, survival rates can be as high as 90% or more. With delays of approximately 7-10 minutes, the survival rate drops to below 10%. Thus, the only effective solution to VF is early defibrillation.

Automatic External Defibrillators (AEDs) can provide early access to defibrillation, but they must be easy-to-use so that they may be administered by a broad range of first responders, portable so they can be easily carried to an SCA victim, and easily maintained so as to ensure high reliability. In addition, AEDs must be affordable, so that they can be broadly deployed and be readily accessible when a SCA event occurs.

AEDs require a portable energy source so as to enable the device to be rapidly deployed to timely treat an SCA victim. Often, the victim may be in a remote or difficult to reach location, making compact and portable AEDs most useful to police, emergency medical services (EMS), Search-And-Rescue teams and other rescue or emergency services.

AEDs must remain in a standby mode for extended periods of time and still be able to administer full power shocks when called upon for use. Most current AEDs are designed to be able to remain in standby mode for a period of two years and still retain the power to be able to administer the necessary shocks. During this standby period, the device must run self-tests to determine the readiness of the device. These tests must be run in an efficient manner to avoid draining the battery during this standby period.

Many current AEDs run automatic self-tests based on a predetermined test schedule, without taking into account prior device use, time of day, pre-programmed information, operational features and previous events.

Thus, there is a need for a new and improved system and method for performing self-tests in an AED.

SUMMARY OF THE INVENTION

The present invention is a system and method for performing self-tests in an AED.

In accordance with one aspect of the present invention, the AED performs self-tests to ensure proper functionality and device readiness. A status indicator is used to inform the user of device readiness.

In accordance with another aspect of the present invention, the AED contains a controller system that performs the self-tests In accordance with another aspect of the present invention, the controller system contains a microprocessor, memory, an analog-to-digital converter (ADC) and other circuitry to perform the self-tests.

In accordance with another aspect of the present invention, the status indicator provides an audible and/or visual signal to the user, and the nature of the signal may depend on the result of the specific self-test performed.

In accordance with another aspect of the present invention, the status indicator comprises of red and green LEDS, a buzzer, an LCD display and a speaker.

In accordance with another aspect of the present invention, the AED uses an LCD display, voice playback circuitry, an audio amplifier and a speaker as a self-test status indicator and to notify the user of events during different modes of the device operation.

In accordance with another aspect of the present invention, the AED contains a battery, high voltage capacitors, a circuit to charge the capacitors and a circuit to deliver a biphasic waveform during the application of a therapeutic pulse.

In accordance with another aspect of the present invention, the AED contains a set of pads (i.e., electrodes) that are applied directly to the patient from the defibrillator. These pads comprise an electrically conductive hydrogel that adheres to the patient's skin and provides good electrical connectivity to the patient's chest.

In accordance with another aspect of the present invention, the controller system contains Flash, RAM and EEPROM memory.

In accordance with another aspect of the present invention, the expiration dates of the battery and the pads are programmed in memory. The programmed expiration dates are checked against the current date during self-test. The defibrillator status indicator notifies the user when the battery and/or pads have passed their expiration date.

In accordance with another aspect of the present invention, the defibrillator has a removable flash memory card for logging self-test information and results, and for logging information about the device during a rescue.

In accordance with another aspect of the present invention, the defibrillator has power control circuitry that turns the device power on and off in response to signal inputs.

In accordance with another aspect of the present invention, the defibrillator has a real-time clock with an interrupt that enables the power control circuitry to turn on.

In accordance with another aspect of the present invention, the defibrillation system has current overload protection circuitry that limits the peak current delivered to the patient.

In accordance with another aspect of the present invention, the defibrillator contains circuitry that records audio during a rescue.

In accordance with another aspect of the present invention, the defibrillator contains a system monitor circuit that resets the controller system in the event of a microprocessor crash.

In accordance with another aspect of the present invention, the defibrillator contains temperature measurement circuitry.

In accordance with another aspect of the present invention, the defibrillator contains buttons for controlling the defibrillator.

In one form of the present invention, there is provided a defibrillator system comprising:
 a capacitor for storing a charge;
 a charge circuit to charge the capacitor;
 a discharge circuit to discharge the capacitor and deliver a biphasic waveform to a patient;
 user interface controls connected to the charge circuit and the discharge circuit and configured to receive operator instructions and to provide system information to the operator; and
 a microprocessor-based self-test controller for testing the system.

In another form of the present invention, there is provided a defibrillator system comprising:
 a battery;
 a capacitor for storing a charge;
 a charge circuit to charge the capacitor from the battery;
 a discharge circuit to discharge the capacitor and deliver a biphasic waveform to a patient;
 user interface controls connected to the charge circuit and the discharge circuit and configured to receive operator instructions and to provide system information to the operator; and
 a microprocessor-based self-test controller for testing the system.

In another form of the present invention, there is provided a method for operating a defibrillator system, comprising:
 providing a defibrillator system comprising:
 a capacitor for storing a charge;
 a charge circuit to charge the capacitor;
 a discharge circuit to discharge the capacitor and deliver a biphasic waveform to a patient;
 user interface controls connected to the charge circuit and the discharge circuit and configured to receive operator instructions and to provide system information to the operator; and
 a microprocessor-based self-test controller for testing the system; and
 operating the system in standby mode so that the controller tests the system while in standby mode.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 2 is a block diagram of the defibrillator components;

FIG. 3 is a table that shows an example of the defibrillator self-test table and error codes;

FIG. 4 is a table that shows an example of the defibrillator self-test scheduling;

DETAILED DESCRIPTION OF THE PREFERRED EMBODIMENTS

The present invention comprises a system and method for performing self-tests in an AED.

Figure 1:
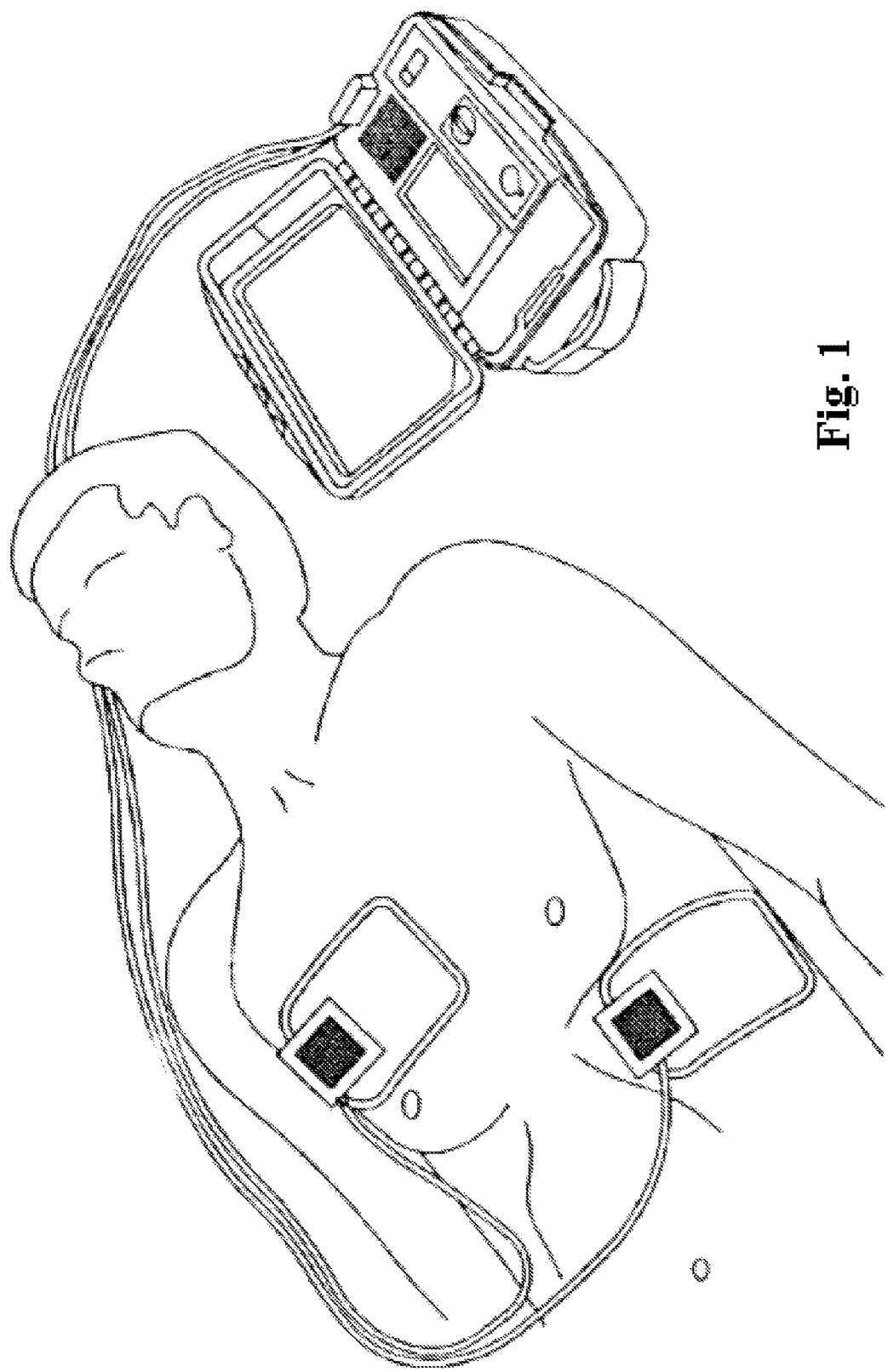
FIG. 1 is a schematic diagram of the defibrillator and electrodes attached to the patient.

As shown in FIG. 1, the patient is connected to the AED via a pair of electrodes, which are attached directly to the skin of the patient's chest. The defibrillator uses the electrodes to provide defibrillation shocks to the patient, where a pulsed electrical current is passed through the patient's heart. The AED also uses the electrodes to first sense ECG signals from the patient so as to determine the condition of the patient's heart (i.e., shockable or not). The electrodes contain a conductive hydogel which secures the pad to the patient's skin and provides good electrical conductivity. The electrodes are terminated with a connector, which is generally connected to the defibrillator after the pads have been applied to the patient.

In a preferred embodiment of the present invention, the electrodes are sealed in a tray, which resides in the lid of the AED. The electrodes are discarded after use and the tray replaced. In one aspect of the invention, the electrodes have a shelf life of 2 years and must thereafter be replaced.

Looking now at FIG. 2, there is shown a block diagram of the AED components. The AED contains a self-test controller system including, but not limited to, a microprocessor (MicroController), programmable logic device (PLD), memory and an analog-to-digital converter (ADC). In one preferred embodiment of the invention, the microprocessor executes instructions to: (i) sample the data; (ii) store the data into memory; and (iii) process the data to perform the self-tests. In the preferred embodiment, the programmable logic device (PLD) controls the interface to the analog-to-digital converter (ADC) and stores the sampled data into a local memory buffer. The programmable logic device (PLD) then interrupts the microprocessor to sample the data contained in the buffer, via a data bus connected between the microprocessor and the PLD. The microprocessor may also directly interface to the analog-to-digital converter (ADC) and use internal timing or interrupts for the sampling frequency. Additionally, the microprocessor may be a microcontroller and have the memory, analog-to-digital converter (ADC) and other peripherals on a single chip.

The analog-to-digital converter (ADC) is connected to circuits which measure a patient's electrocardiogram (ECG), a patient's transthoracic impedance, the AED temperature, the AED's capacitor charger circuits and other circuits discussed below.

In a preferred embodiment of the present invention, the defibrillator contains a removable flash memory card. The defibrillator uses the flash memory card to store pertinent data. Examples of such data include, but are not limited to, ECG data, self-test results, environment data, device use data, diagnostic information and other relevant data discussed below.

In a preferred embodiment of the present invention, the flash memory card is a multi-media card. In other preferred embodiments, the flash memory card may be CompactFlash, synchronous digital or similar flash card types.

The AED also contains the conventional electrical components used to generate defibrillation shocks including, but not limited to, a battery pack, capacitor charger circuit, high-voltage capacitors and an H-bridge circuit.

The battery pack is connected to the analog-to-digital converter (ADC) through a voltage divider. The battery voltage can, therefore, be measured during self-test.

The defibrillator also contains an LCD screen, voice synthesizer and speaker for instructing the rescuer during device use. The voice synthesizer and speaker are also capable of producing tones. These components are also used for the status indicator system. The LCD screen and tones are used to notify the user of the self-test result, a potential user action to take and an error code if a critical self-test has failed. An example of a potential user action is to replace a depleted battery before attempting to defibrillate a patient. Another example of a user action is to replace out-of-date pads before placing the device back in to service.

In a preferred embodiment of the present invention, the status indicator system also includes a buzzer, a green LED and a red LED.

The defibrillator also contains a number of buttons for user control. These buttons include, but are not limited to, a power button, a shock button and one or more special purpose buttons. A preferred embodiment of the present invention includes buttons to manually control the defibrillator.

The defibrillator also contains an audio recording circuit that is used to record rescuer's voices and other audible events. The audio recording circuit contains a small microphone and a digital recording integrated circuit (IC), which compresses and buffers the audio data. The controller system reads the data from the recording IC's buffer and stores the data on the removable flash card.

During self-tests, the defibrillator checks the analog circuits, the components (e.g., the battery), the peripherals (e.g., the pads), memory and other relevant devices or circuits.

In a preferred embodiment of the present invention, the self-test circuitry comprises a controller, e.g., a microcontroller that has many peripherals on chip. Hence, the controller is capable of testing itself. As those skilled in the art can appreciate, the device uses industry standard techniques, such as cyclical redundancy checks (CRC), on all memory devices (e.g., Flash ROM, RAM, EEPROM and external flash).

The defibrillator contains a system monitor that resets the system in the event of a microcontroller crash. In a preferred embodiment of the present invention, the monitor is a "watchdog-timer" type circuit which must be periodically reset. If the circuit is not reset, it will begin sending non-maskable interrupts (NMIs) to the microcontroller. If the interrupt is serviced, the system can recover and continue normal operation. If the interrupts are not serviced, the monitor circuit considers the system unstable, and produces a system reset, which causes the defibrillator to reboot and run through a power-on self-test.

In a preferred embodiment of the present invention, the defibrillator contains in analog-to-digital converter (ADC), which has internal and external reference voltages which are tested by the self-test controller.

In a preferred embodiment of the present invention, the self-test controller tests the capacitor charging circuit by initiating a charging cycle of the capacitors. The self-test controller monitors the charging rate and applies boundaries while the capacitors are charging. The capacitors are charged to a test level. If the charger circuit does not charge at the correct rate, or cannot reach the appropriate charge level, then the test fails.

In a preferred embodiment of the present invention, the capacitors are charged to 50V during testing. The charge on the capacitors is subsequently dumped (i.e., safely discharged) when the test is complete.

As is well known in the art, it is important to detect low battery capacity in defibrillators. This is because the AED may remain in standby mode for several years, and/or have been previously used, either of which could result in a low-battery capacity which could inhibit proper charging of the capacitors. In a preferred embodiment of the invention, the battery pack consists of several Lithium Manganese Dioxide battery cells. As those skilled in the art can appreciate, it is difficult to determine the remaining battery capacity of these cell types without applying a load or, in other words, when drawing a considerable amount of current from the battery, such as an ampere or more. Hence, the aforementioned charging circuit test also yields information about the remaining battery capacity. In a preferred embodiment of the present invention, the self-test controller uses an algorithm to determine when the battery pack is at low capacity.

In a preferred embodiment of the present invention, the battery pack has a "Replace Before" date printed on the battery label. This date is essentially an expiration date printed on the pack along with the date of manufacture. This expiration date is also programmed into the controller's flash memory. During self-test, the programmed expiration date is checked against the current date contained in the AED's real-time clock. The defibrillator status indicator notifies the user when the battery has expired.

In a preferred embodiment of the present invention, the electrode tray has a "Use Before" date printed on the tray label. This date is essentially an expiration date printed on the tray along with the date of manufacture. This expiration date is also programmed into the controller's flash memory. During self-test, the programmed expiration date is checked against the current date contained in the AED's real-time clock. The defibrillator status indicator notifies the user when the electrode tray has expired.

The defibrillator also contains a circuit to measure the internal device temperature. In a preferred embodiment of the present invention, the temperature circuit consists of a negative temperature coefficient thermistor. The self-test controller logs the device temperature onto the flash card.

In a preferred embodiment of the present invention, the defibrillator contains a voice synthesizer IC, which is programmed with messages to guide the user through operation of the device. The self-test controller tests the functionality of the voice synthesizer IC.

In a preferred embodiment of the present invention, the defibrillator contains an audio recording circuit capable of recording the rescuer's voice and audible events during a rescue. The self-test controller tests the functionality of the audio recording circuit. In one aspect of the present invention, the audio recording feature is an optional feature of the device. The self-test controller has a configuration menu which permits enabling or disabling the test for the optional audio recording feature. The self-test controller conditionally tests the optional audio recording feature based on the configuration menu.

The defibrillator also contains buttons for controlling the defibrillator. In a preferred embodiment of the present invention, the buttons are dome-type buttons. The self-test controller tests for broken or stuck switches.

In a preferred embodiment of the present invention, the defibrillator contains a circuit for detecting over-current during a discharge. As those skilled in the art can appreciate, it is important to limit the peak current during discharge to avoid myocardial damage. In another aspect of the present invention, it is important to detect over-current in the event of a short circuit between the two pads in order to avoid damaging the defibrillator's high-voltage circuitry.

In a preferred embodiment of the present invention, the defibrillator contains a secondary safety circuit that enables the charger and H-bridge circuits. The self-test controller tests that this circuit can enable and disable the charger and H-bridge circuits.

In a preferred embodiment of the invention, if the self-test is completed without failure, the device notifies the user (i.e., on the LCD) "Self-Test Pass" accompanied by a single tone on the speaker. If the self-test detects an error, the device notifies the user (i.e., on the LCD) "Self-Test Failed XXXX" accompanied by a three tones on the speaker. FIG. 3 shows examples of such XXXX error codes.

AEDs typically run in the standby mode for extended periods of time. During this period, the device must run self-tests to determine the readiness of the device. In one aspect of the invention, the defibrillator runs a daily self-test. Alternatively, the defibrillator could be configured to periodically run the self test based on another time interval, e.g., weekly, bi-weekly, etc.

In another aspect of the invention, the defibrillator runs a power-on self-test whenever the device has been powered-on by the user (i.e., by pressing the power button).

In a preferred embodiment of the invention, the real-time clock has an interrupt that signals the power control circuit to turn the device on. The self-test controller contains a programmed self-test "wake-up" time in the configuration flash memory. In a preferred embodiment of the invention, the defibrillator conditionally runs the self-test if the controller matches the current time of day in the real-time clock with the wake-up time in memory. In other words, the defibrillator runs the self-test when current time (indicated by the real-time clock) matches the wake-up time (stored in the memory). In one aspect of the invention, if the current time does not match the wake-up time, the device powers off. In another aspect of the invention, if the current time does not match the wake-up time, the device defaults to a power-on self-test. In another aspect of the invention, if the real-time clock does not indicate that a wake-up has occurred in its internal status register, the device defaults to a power-on self-test.

In another aspect of the present invention, the defibrillator will run in standby mode for two years without operator intervention, which is equivalent to the standby life of the battery pack and electrodes.

While in standby mode, the device must run self-tests in an efficient manner so as to avoid excessively draining the battery and thereby rendering it unreliable before the expiration date. In a preferred embodiment of the invention, the controller runs daily self-tests, conditionally, utilizing knowledge of prior device use, time of day, pre-programmed information, operational features and previous events.

In a preferred embodiment of the invention, the controller runs daily self-tests, conditionally, using a schedule. In another preferred embodiment of the invention, the schedule is run over a four-day period as shown in FIG. 4. The defibrillator maximizes test coverage over this period, without sacrificing battery capacity.

In another preferred embodiment of the invention, the controller runs a power-on self-test when the user has pressed the power button. In one particular form of the present invention, the self-test controller runs all of the aforementioned self-tests conditionally in the power-on self-test.

Figure 5:
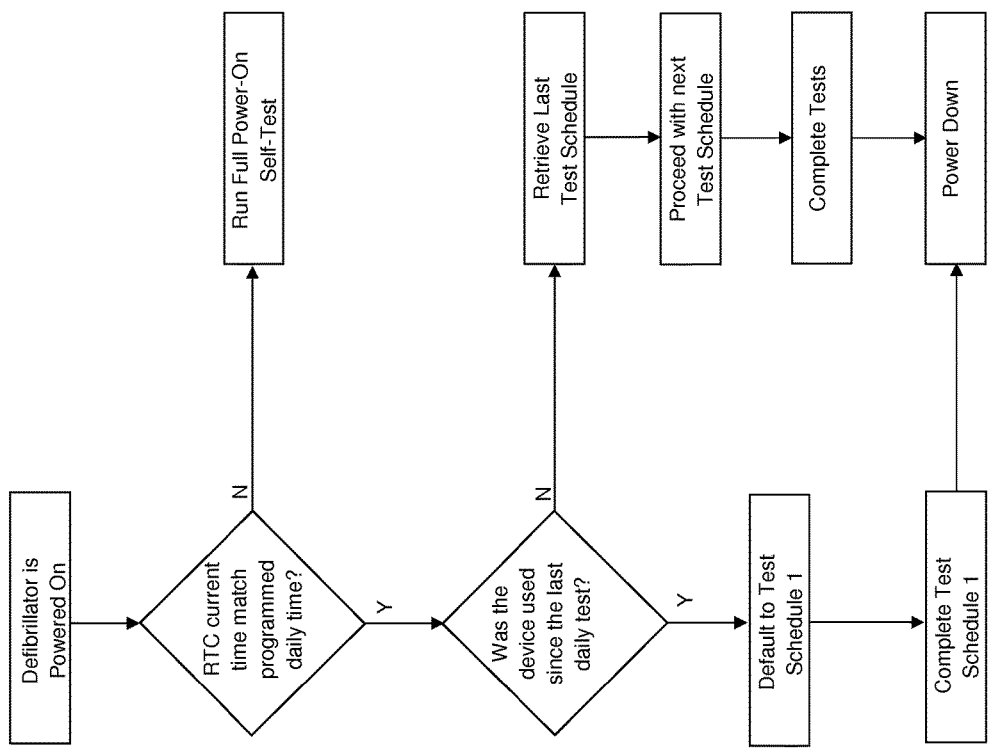
FIG. 5 is a flow diagram that shows an example of the defibrillator conditional self-test system.

A flow diagram is shown in FIG. 5 and provides an example of the defibrillator conditional self-test system. In this form of the invention, the defibrillator only runs the daily test if the current time in the real time clock matches the pre-programmed daily wake-up time stored in memory. The self-test controller conditionally reschedules the tests based on device usage. In a preferred embodiment of the invention, the self-test controller schedules the battery capacity and capacitor charging circuit tests first if the device has previously been used. It will be appreciated that the importance of such tests may increase in cases where the device has been previously used.

Figure 6:
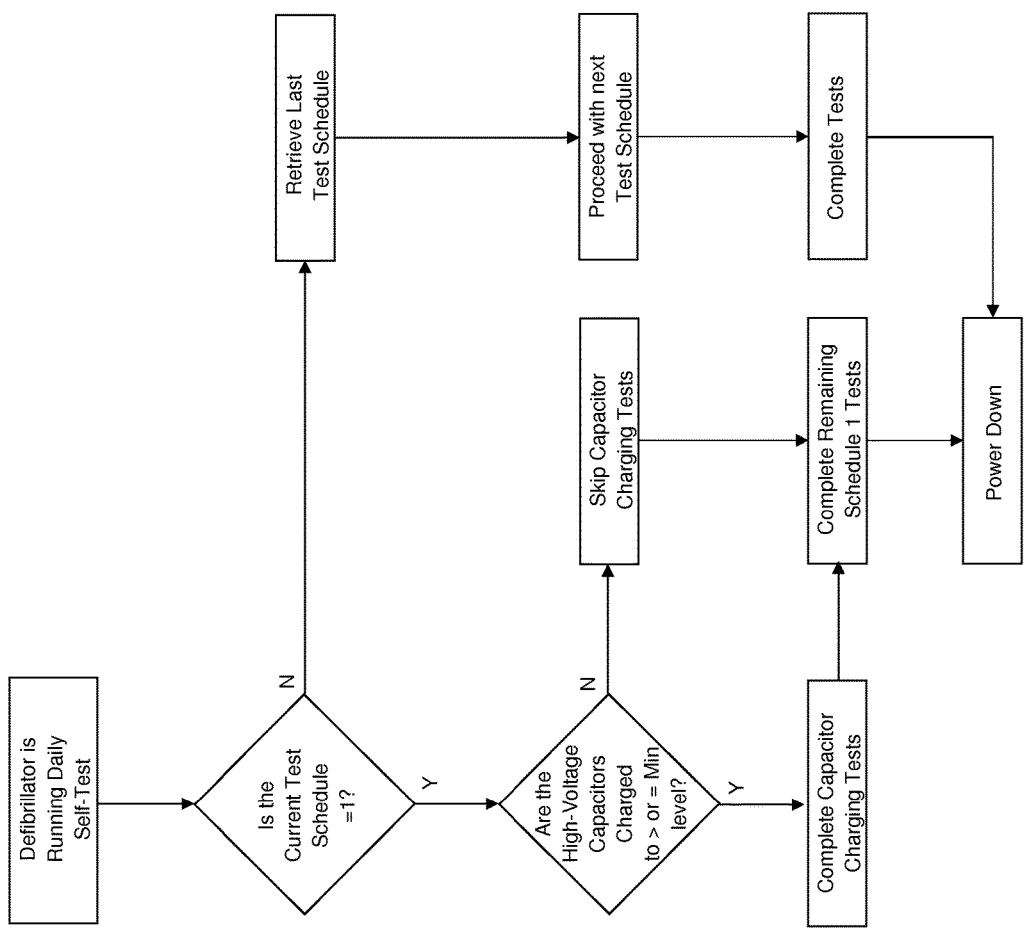
FIG. 6 is a flow diagram that shows an example of a conditional self-test sub-system based on knowledge of defibrillator use.

A flow diagram is shown in FIG. 6 and provides an example of a conditional self-test sub-system based on knowledge of prior defibrillator use. In one preferred embodiment of the invention, the self-test controller conditionally runs the self-test based on the charge level of the high-voltage capacitors.

Figure 7:
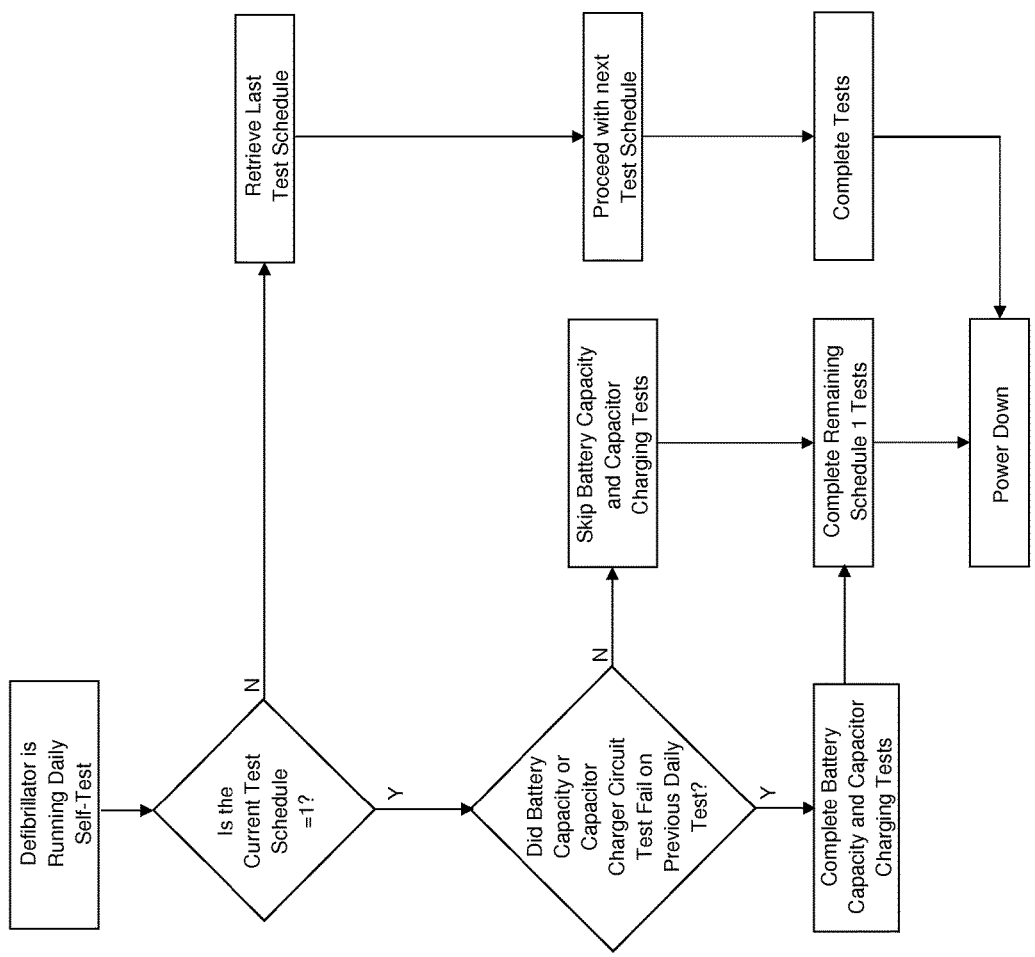
FIG. 7 is a flow diagram that shows an example of a conditional self-test sub-system based on previous events of the defibrillator.

A flow diagram is shown in FIG. 7 and provides an example of a conditional self-test sub-system based on previous events of the defibrillator. In a preferred embodiment of the invention, the self-test conditionally runs the battery capacity and capacitor charger circuit tests only if the device has not previously failed a self-test. Such a mode of operation can be important, since running these tests after the battery has already failed a self-test will have the effect of depleting the already-questionable battery capacity even further. It should be noted that the flag set during the daily test is cleared once the defibrillator runs through a full power-on.

Figure 8:
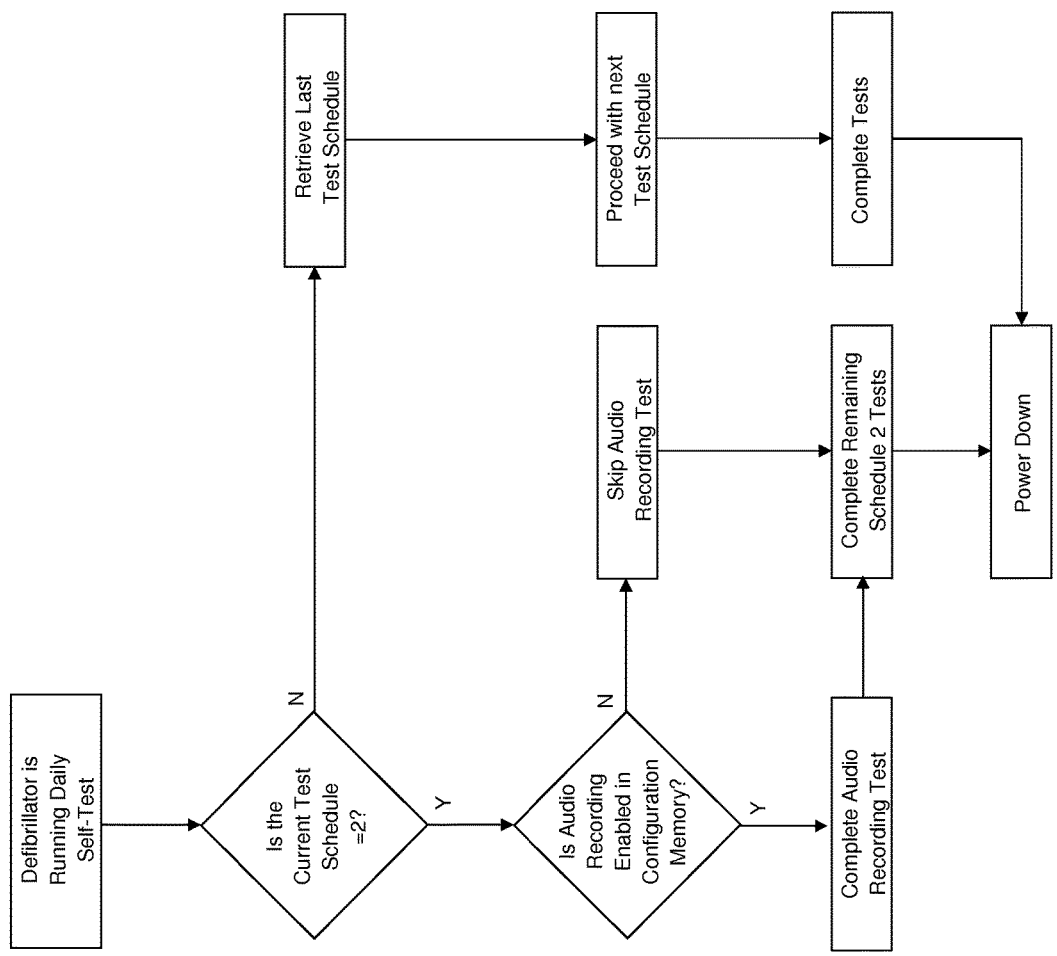
FIG. 8 is a flow diagram that shows an example of a conditional self-test sub-system based on pre-programmed device configuration of the defibrillator.

A flow diagram is shown in FIG. 8 and provides an example of a conditional self-test sub-system based on a pre-programmed configuration for the defibrillator. In a preferred embodiment of the invention, the self-test controller conditionally runs tests if the device is configured for such features. In this respect it will be appreciated that those skilled in the art that many AEDs are marketed with optional features so as to meet the demands of different markets; thus, the configuration shown in FIG. 8 permits the self-test to be configured in accordance with a specific set of product features.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A defibrillator system comprising:
   a battery having a battery capacity;
   a capacitor for storing a charge;
   a charge circuit to charge the capacitor from the battery;
   a discharge circuit to discharge the capacitor and deliver a biphasic waveform to a patient;
   user interface controls connected to the charge circuit and the discharge circuit and configured to receive operator instructions and to provide system information to the operator; and
   a microprocessor-based self-test controller for testing the system;
   wherein the microprocessor-based self-test controller periodically initiates a test of the defibrillator system to determine (i) whether the battery capacity is below a predetermined threshold value, and (ii) whether the capacitor charge circuit is functioning within predetermined parameters;
   and further wherein the microprocessor-based self-test controller only runs the battery capacity test and the capacitor charge circuit test if the defibrillator system has not previously failed a self-test.

2. A system according to claim 1 wherein the user interface controls comprise at least one element from the group consisting of:
   an LCD display;
   an LED;
   a buzzer;
   a voice playback circuit;
   an audio amplifier; and
   an audio speaker to notify the operator of events during system operation.

3. A system according to claim 1 wherein the battery is part of a battery pack.

4. A system according to claim 1 wherein the system further comprises a pair of electrode pads.

5. A system according to claim 1 wherein the controller further conditionally runs tests based on prior system use.

6. A system according to claim 5 wherein the prior system use comprises at least one event from the group consisting of:
   a prior capacitor discharge;
   the number of prior capacitor discharges;
   the time interval since the last capacitor discharge;
   the number of times the system was previously powered on; and
   the number of previous self-tests performed.

7. A system according to claim 5 wherein the controller further conditionally runs tests based on at least one from the group consisting of:
   a pre-programmed system parameter;
   system configuration; and
   prior events.

8. A system according to claim 1 wherein the controller further conditionally runs tests based on a pre-programmed system parameter.

9. A system according to claim 8 wherein the pre-programmed system parameter comprises at least one parameter from the group consisting of:
   a voltage level;
   a rate of charge;
   a "Replace Before" date;
   a "Use Before" date; and
   a temperature limit.

10. A system according to claim 8 wherein the controller further conditionally runs tests based on at least one from the group consisting of:
    prior system use;
    system configuration; and
    prior events.

11. A system according to claim 1 wherein the controller further conditionally runs tests based on system configuration.

12. A system according to claim 11 wherein system configuration comprises at least one feature from the group consisting of:
    a voice synthesizer;
    the presence of a flash card;
    the manual override controls; and
    audio recording circuit.

13. A system according to claim 11 wherein the controller further conditionally runs tests based on at least one from the group consisting of:
    prior system use;
    a pre-programmed system parameter; and
    prior events.

14. A system according to claim 1 wherein the controller further conditionally runs tests based on prior events.

15. A system according to claim 14 wherein the prior event comprises at least one event from the group consisting of:
    the length of time the system has remained in standby mode;
    a previous test outcome;
    the occurrence of over-current during discharge;
    use of the system since a previous self-test; and
    temperature.

16. A system according to claim 14 wherein the controller further conditionally runs tests based on at least one from the group consisting of:
    prior system use;
    a pre-programmed system parameter; and
    system configuration.

17. A system according to claim 1 wherein the controller includes an algorithm to determine the battery capacity without applying a load to the battery.

18. A system according to claim 1 wherein the controller includes an algorithm to determine the battery capacity while applying a load to the battery.

19. A method for operating a defibrillator system, comprising:
    providing a defibrillator system comprising:
      a battery having a battery capacity;
      a capacitor for storing a charge;
      a charge circuit to charge the capacitor from the battery;
      a discharge circuit to discharge the capacitor and deliver a biphasic waveform to a patient;
      user interface controls connected to the charge circuit and the discharge circuit and configured to receive operator instructions and to provide system information to the operator; and
      a microprocessor-based self-test controller for testing the system;
      wherein the microprocessor-based self-test controller periodically initiates a test of the defibrillator system to determine (i) whether the battery capacity is below a predetermined threshold value, and (ii) whether the capacitor charge circuit is functioning within predetermined parameters;

and further wherein the microprocessor-based self-test controller only runs the battery capacity test and the capacitor charge circuit test if the defibrillator system has not previously failed a self-test; and operating the system in standby mode so that the controller tests the system while in standby mode.

20. A method according to claim 19 wherein the controller further conditionally tests the system.

\* \* \* \* \*